US011684682B2

(12) United States Patent
Baranyai et al.

(10) Patent No.: US 11,684,682 B2
(45) Date of Patent: Jun. 27, 2023

(54) CHELATING AAZTA CONJUGATES AND COMPLEXES THEREOF

(71) Applicant: BRACCO IMAGING S.P.A., Milan (IT)

(72) Inventors: Zsolt Baranyai, Trieste (IT); Simona Ghiani, Turin (IT); Alessandro Maiocchi, Monza (IT); Ivan Hawala, Turin (IT)

(73) Assignee: BRACCO IMAGING S.P.A., Milan (IT)

( * ) Notice: Subject to any disclaimer, the term of this patent is extended or adjusted under 35 U.S.C. 154(b) by 193 days.

(21) Appl. No.: 17/292,479

(22) PCT Filed: Nov. 12, 2019

(86) PCT No.: PCT/EP2019/081014
§ 371 (c)(1),
(2) Date: May 10, 2021

(87) PCT Pub. No.: WO2020/099398
PCT Pub. Date: May 22, 2020

(65) Prior Publication Data
US 2022/0016275 A1    Jan. 20, 2022

(30) Foreign Application Priority Data

Nov. 12, 2018  (EP) .................................. 18205796

(51) Int. Cl.
*A61K 51/08*   (2006.01)
*A61P 35/00*   (2006.01)
*C07K 7/64*    (2006.01)

(52) U.S. Cl.
CPC .............. *A61K 51/08* (2013.01); *A61P 35/00* (2018.01); *C07K 7/64* (2013.01)

(58) Field of Classification Search
CPC ............ A61K 51/08; A61P 35/00; C07K 7/64
See application file for complete search history.

(56) References Cited

FOREIGN PATENT DOCUMENTS

| WO | 2003008390 | A1 |   | 1/2003 |
|----|------------|----|---|--------|
| WO | 2006002873 | A2 |   | 1/2006 |
| WO | 2006136564 | A1 |   | 12/2006 |
| WO | 2008071679 | A1 |   | 6/2008 |
| WO | WO 2008071679 |  | * | 6/2008 |
| WO | 2013135750 | A1 |   | 9/2013 |
| WO | WO 213135750 |  | * | 9/2013 |

OTHER PUBLICATIONS

Anncatrine L. Petersen et al. Positron emission tomography evaluation of somatostatin receptor targeted 64—(Year: 2012).*

Akitt, et al., "71Ga Nuclear Magnetic Resonance Investigation of Aqueous Gallium(III) and its Hydrolysis," Mag. Res. Chem. 27:377-379(1989).
Baranyai, et al., "Equilibrium, Kinetic and Structural Studies of AAZTA[‡] Complexes with Ga3+, In3+ and Cu2+," Eur. J. Inorg. Chem., 2013:147-162 (2013).
Broan, C.J. et al., "Structure and Solution Stability of Indium and Gallium Complexes of 1,4,7-Triazacyclononanetriacetate and of Yttrium Complexes of 1,4,7,10-Tetraazacyclododecanetetraacetate and Related Ligands: Kinetically Stable Complexes for Use in Imaging and Radioimmunotherapy. X-Ray Molecular Structure of the Indium and Gallium Complexes of 1,4,7-Triazacyclononane-I , 4,7-triacetic Acid," J. Chem. Soc. Perkin Trans. 2:87-99 (1991).
Chang, et al., "Determination of Stability Constants of Metal Complexes by Capillary Electrophoresis," Chinese. Chem. Soc., 46:519-528 (1999).
International Search Report and Written Opinion for PCT/EP2019/081014, dated Jan. 17, 2020.
Irving, H. M. et al., "A study of some problems in determining the stoicheiometric proton dissociation constants of complexes by potentiometric titrations using a glass electrode," Anal. Chim. Acta, 38:475-488 (1967).
Karadakov, et al., "The complexes of bismuth(III) and nitrilotriacetic acid," Talanta, 17:878-883 (1970).
Kornev, et al., "The stability of bismuth(III) complexonates in aqueous solution," Russ. J. Inorg. Chem, 32:1419-1421 (1987).
Kwekkeboom, et al. "Somatostatin-receptor-based imaging and therapy of gastroenteropancreatic neuroendocrine tumors," Endocrine-Related Cancer, 17:R53-R73 (2010).
Ma, et al., "Rapid kit-based (68)Ga-labelling and PET imaging with THP-Tyr(3)-octreotate: a preliminary comparison with DOTA-Tyr(3)-octreotate," EJNMMI Research, 5:52 (2015).
Manzoni et al., "Synthesis of Gd and (68)Ga complexes in conjugation with a conformationally optimized RGD sequence as potential MRI and PET tumor-imaging probes," ChemMedChem, 7:1084-1093 (2012) and Supporting Information.
Nagel, J., "Synthase, Radiomarkierung sowie in vitro- und in vivo—Evaluierung verschiedener Chelator-Biomolekul-Systeme mit den Radionukliden 68Ga, 89Zr und 177Lu," Dissertation, pp. 1-246, available at: https://d-nb.info/1140168274/34 (retrieved on May 5, 2021) (2017).

(Continued)

*Primary Examiner* — Michael G. Hartley
*Assistant Examiner* — Jagadishwar R Samala
(74) *Attorney, Agent, or Firm* — Vivicar Law, PLLC

(57) ABSTRACT

A chelating compound of formula (I) or a pharmaceutically acceptable salt thereof and its complexes with metals or radioisotopes thereof. The invention further relates to the preparation of such ligand and complexes as well as to their use as diagnostic or therapeutic agents.

19 Claims, No Drawings

(56) References Cited

OTHER PUBLICATIONS

Nagy et al., "AAZTA: An Ideal Chelating Agent for the Development of 44 Sc PET Imaging Agents," Angew Chem. Int. Ed. Engl., 56(8):2118-2122 (2017).

Nock et al., "Novel bifunctional DATA chelator for quick access to site-directed PET 68 Ga-radiotracers: preclinical proof-of-principle with [Tyr 3]octreotide," Dalton Trans., 46:14584-14590 (2017).

Oe, et al., "Effects of anion binding on the conformations of the two domains of ovotransferrin," J. Biochem, 106:858-863 (1989).

Petersen, et al., "Positron emission tomography evaluation of somatostatin receptor targeted 64Cu-TATE-liposomes in a human neuroendocrine carcinoma mouse model," J. Control. Release, 160:254-263 (2012).

Pfister, et al. "Influence of a novel, versatile bifunctional chelator on theranostic properties of a minigastrin analogue," EJNMMI Res., 5:74 (2015).

Price, et al. "Matching chelators to radiometals for radiopharmaceuticals," Chem. Soc. Rev., 43:260-290 (2014).

Sinnes et al, "AAZTA-5-PSMA: Kit-type radiolabeling with 44Sc and 177Lu and first in vitro affinity studies," J. Nucl. Med., 58(1):670 (2017).

Sinnes, et al., "AAZTA-5: a new kit-type chelator for Lu-177 and Sc-44 with theranostic application in conjunction with DATA-5m for Ga-68," J. Nucl. Med., 57(2):1069 (2016).

Tóth, et al., Equilibrium Study of the Systems of Aluminium(III), Gallium(III) and Indium(III) With Mercaptoacetate, 3-Mercaptopropionate and 2-Mercaptobenzoate, Polyhedron, 3:871-877 (1984).

Velikyan, et al., "Convenient preparation of 68Ga-based PET-radiopharmaceuticals at room temperature," Bioconjugate Chem., 19:569-573 (2008).

World Health Organization, "Radiopharmaceuticals, Final text for addition to The International Pharmacopoeia," Document QAS/08.262/FINAL, available at https://www.who.int/medicines/publications/pharmacopoeia/Radgenmono.pdf (2008).

Wu et al., "New (68)Ga-PhenA bisphosphonates as potential bone imaging agents," Nuclear Medicine and Biology, 43:360-371 (2016).

Young et al. "68Ga-THP-PSMA: A PET Imaging Agent for Prostate Cancer Offering Rapid, Room-Temperature, 1-Step Kit-Based Radiolabeling," J Nucl Med., 58(8): 1270-1277 (2017).

Zékány, et al., "PSEQUAD: A comprehensive program for the evaluation of potentiometric and/or spectrophotometric equilibrium data using analytical derivatives," In: Computational Method for Determination of Formation Constants, Ed. Legett DJ, Plenum, New York, pp. 291-353 (1985).

Communication pursuant to Article 94(3) EPC in European App. No. 19801028.2, dated Apr. 19, 2022.

\* cited by examiner

CHELATING AAZTA CONJUGATES AND COMPLEXES THEREOF

CROSS-REFERENCE TO RELATED APPLICATIONS

This application is the national stage application of corresponding international application number PCT/EP2019/081014, filed Nov. 12, 2019, which claims priority to and the benefit of European application no. 18205796.8, filed Nov. 12, 2018, which is hereby incorporated by reference in its entirety.

TECHNICAL FIELD

The present invention generally relates to the field of Nuclear medicine (NM). In particular, it relates to a new conjugate of the chelator 6-amino-6-methylperhydro-1,4-diazepinetetraacetic acid with ([Tyr3] octreotate/D-phenylalanyl-L-cysteinyl-L-tyrosyl-D-tryptophyl-L-lysyl-L-threonyl-L-cysteinyl-L-threonine cyclic disulfide (a SSTR agonist) and its complexes with metals or radioisotopes thereof. The invention further relates to the preparation of such ligand and complexes as well as to their use as diagnostic or therapeutic agents.

BACKGROUND OF THE INVENTION

Radiopharmaceuticals are unique medicinal formulations containing radioisotopes which are used in major clinical areas for diagnosis and/or therapy. For biological applications, metallic radionuclides are most commonly coordinated with chelators (ligands) for safe administration. Furthermore, ligands typically used to construct radiometal-based radiopharmaceuticals are bifunctional chelators (BFCs), with reactive functional group(s) that can be covalently coupled (conjugated) to targeting vectors (e.g. peptides, nucleotides, antibodies, nanoparticles), in order to obtain a target-specific activity showing affinity and selectivity for the selected target. In this way, while the chelator tightly binds a radiometal ion when injected into a patient, the targeting molecule can deliver the isotope without any radiometal loss from the radiopharmaceutical, effectively supplying a site-specific radioactive source in vivo for imaging or therapy (Price, Chem. Soc. Rev., 2014, 43, 260). The use of a radiometal lends itself to a quick single-step complexation to prepare the diagnostic probe, compared to the long (multistep) synthesis required for introducing relatively short-lived $^{18}F$ or $^{11}C$ within the molecular backbone. Chelators can be classified into open-chain/acyclic (EDTA (Ethylenediaminetetraacetic acid), DTPA (Diethylene triamine pentaacetic acid)) and their derivatives) and macrocyclic (NOTA (2-[4,7-bis(carboxymethyl)-1,4,7-triazonan-1-yl]acetic acid), DOTA ((1,4,7,10-Tetraazacyclododecane-1,4,7,10-tetraacetic acid)) and their derivatives). Among the current chelators, DOTA is one of the primary workhorse ligands for radiometal chemistry and is one of the current "gold standards" for a number of isotopes, including $^{68}Ga$, $^{111}In$, $^{177}Lu$, $^{86/90}Y$, $^{225}Ac$, and $^{44/47}Sc$. DOTA has been extensively used, and it has already been approved by FDA in two different products for nuclear medicine, NETSPOT® (Ga-68 DOTATATE) and LUTATHERA® (Lu-177 DOTATATE), commercialized by Advanced Accelerator Applications USA INC. (now Novartis Company). Notwithstanding its interesting advantages, such as the easy commercial access to the variety of bifunctional intermediates, its use is restricted to temperature tolerable targeting moieties, due in particular to the very slow formation rate of the DOTA complexes and drastic reaction conditions. Serious limitations of DOTA have prompted many centers around the world to develop new chelators and currently this is among highly researched areas in the field of radiopharmaceuticals. Another drawback that emerged from the analysis of the state of the art is associated to the current radiolabeling method. Radiolabeling for temperature sensitive biologically active moieties (e.g. peptides, minibodies, antibodies, etc.) can for instance be performed in a two-step process. The first step involves the labeling of the bifunctional chelates with radiometals at high temperature, while the second step is conjugation of the radioactive complex with the biologically active moiety at lower (e.g. ambient/room) temperature followed by purification. This two-step process may cause further loss of the radioactivity. In order to overcome these difficulties, alternative chelators, mainly for $^{68}Ga$, to produce "kit-type" labeling reagents have been proposed (such as DATA-TOC, see for instance Nock et al. Dalton Trans. 2017, 46(42), 14584-14590; or THP-TATE, see for instance Ma et al. EJNMMI Research, 2015, 5:52; or NODAGA-TATE, see for instance Velikyan, Bioconjugate Chem. 2008, 19, 2, 569-573; THP-PSMA, see for instance Young, J Nucl Med., 2017, 58(8): 1270-1277), which could be used for the preparation of other radiometal based radio-diagnostic/radiotherapeutic agents at room temperature and near physiological condition, preferably in a single step process.

AAZTA (6-amino-6-methylperhydro-1,4-diazepinetetraacetic acid) has the following formula:

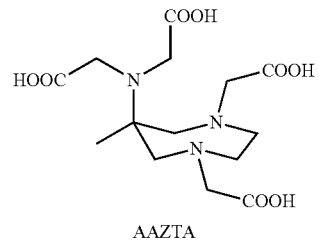 [SMILES: CC1(N(CC(=O)O)CC(=O)O)CN(CC(=O)O)CCN(CC(=O)O)C1]

AAZTA

AAZTA and AAZTA derivatives are disclosed for instance in International Patent Applications WO2003/008390, WO2006/136564, WO2006/002873, WO2013/135750 and WO2008/071679 (BRACCO Imaging SpA). Bifunctional AAZTA derivatives are disclosed in a number of papers, such as, for instance Nagy et al, Angew. Chem. Int. Ed., 2017; Sinnes et al, J Nucl Med, 2017; Sinnes et al, J Nucl Med, 2016; Pfister et al., EJNMMI Res., 2015, 5(1):74; Wu Z. et al., Nuclear Medicine and Biology, 43, 6, 2016, 360-371.

The synthesis of novel chelates of Gd and $^{68}$Ga with several chelators, among which AAZTA, DTPA, DOTA, HP-DOA3 (2-[4,7-bis(carboxylatomethyl)-10-(2-hydroxypropyl)-1,4,7,10-tetrazacyclododec-1-yl]acetate), in conjugation with a conformationally optimized RGD sequence as potential MRI and PET Tumor-Imaging Probes was studied by Manzoni and colleagues (Manzoni et al. ChemMedChem, 7, 2012, 1084-1093).

([Tyr3] octreotate/D-phenylalanyl-L-cysteinyl-L-tyrosyl-D-tryptophyl-L-lysyl-L-threonyl-L-cysteinyl-L-threonine cyclic disulfide (TATE) is a peptide of formula:

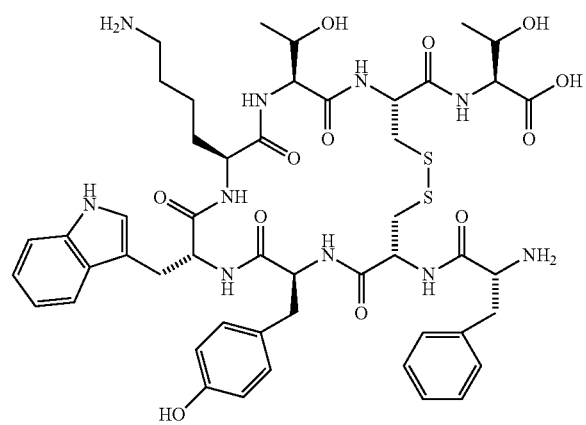

known for being a somatostatin receptors (SSTR)-agonist.

SSTRs are found with high density in numerous malignancies, including gastroenteropancreatic neuroendocrine tumors (GEP-NET), CNS, breast, lung, and lymphatics while low density has been found in kidney, medullary thyroid, prostate and colon. The role of SSTR agonists in neuroendocrine tumours (NETs) is well established and massive SSTR overexpression is present in several NETs. SSTR is a proven NET target/biomarker (Kwekkeboom et al, Endocrine-Related Cancer, 2010, 17 R53-R73).

Applicant has now found a new peptide-conjugated AAZTA derivative including AAZTA ligand and molecular vector TATE.

As observed by the Applicant the metal complexes of the new probe AAZTA-TATE have unexpected improved in vivo properties with respect to corresponding metal complexes of DOTA-TATE.

Applicant has further observed that the metal complexes prepared with the bioconjugate of the invention comprising AAZTA and TATE possess surprisingly high kinetic inertness. In particular, the bioconjugates ligands of the invention are unexpectedly more stable than their corresponding non-bioconjugated complexes of AAZTA.

This new conjugate and respective metal complexes are suitable as a new tool for diagnosing and treating pathologies, in particular associated with SSTR expression.

SUMMARY OF THE INVENTION

An aspect of the present invention relates to a compound having formula (I):

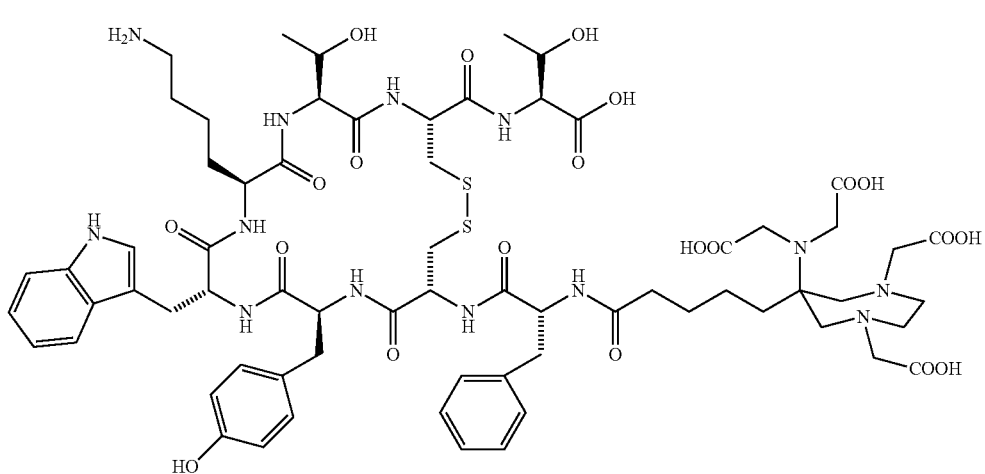

(I)

or a pharmaceutically acceptable salt thereof.

The invention further relates to a metal complex comprising the chelating compound of formula (I), or its pharmaceutically acceptable salt, and a metal ion.

The compound of formula (I) can be complexed with an ion of a metal atom selected from $^{43}$Sc, $^{44}$Sc, $^{44m}$Sc, $^{47}$Sc, $^{51}$Cr, $^{52}$Fe, $^{52}$Mn, $^{52m}$Mn, $^{55}$Co, $^{58}$Co, $^{60}$Cu, $^{61}$Cu, $^{62}$Cu, $^{64}$Cu, $^{67}$Cu, $^{67}$Ga, $^{68}$Ga, $^{72}$As, $^{86}$Y, $^{88}$Y, $^{90}$Y, $^{97}$Ru, $^{99m}$Tc, $^{103}$Ru, $^{105}$Rh, $^{109}$Pd, $^{111}$In, $^{111}$Ag, $^{112}$Ag, $^{117m}$Sn, $^{140}$La, $^{141}$Ce, $^{142}$Pr, $^{149}$Pm, $^{149}$Tb, $^{152}$Tb, $^{155}$Tb, $^{153}$Sm, $^{159}$Gd, $^{161}$Tb, $^{165}$Dy, $^{166}$Dy, $^{166}$Ho, $^{167}$Tm, $^{168}$Yb, $^{175}$Yb, $^{177}$Lu, $^{186}$Re, $^{188}$Re, $^{199}$Au, $^{203}$Pb, $^{212}$Pb, $^{205}$Bi, $^{206}$Bi, $^{210}$Bi, $^{211}$Bi, $^{212}$Bi, $^{213}$Bi and $^{214}$Bi.

The metal ion is preferably selected from an ion of $^{44}$Sc, $^{47}$Sc, $^{68}$Ga, $^{177}$Lu, $^{212}$Pb or $^{213}$Bi.

A further aspect of the invention relates to the use of this chelating compound as a diagnostic imaging agent (e.g. PET/SPECT imaging) or as therapeutic agent (e.g. alpha/beta/Auger), particularly for the diagnosis or treatment of neuroendocrine tumors.

The present invention further relates to a method for the preparation of the compound of formula (I) comprising the synthesis of the compound of formula (I) and its subsequent complexation with one of the selected metal ions. In general, when the metal ion is a radionuclide, the complexation is also identified as "radiolabelling".

According to another aspect, the invention relates to a radiopharmaceutical composition suitable for the PET/SPECT imaging comprising the compound of formula (I), particularly when radiolabeled with $^{68}$Ga or $^{44}$Sc, or suitable for therapeutic purposes, preferably when the compound of formula (I) is radiolabeled with $^{213}$Bi, $^{47}$Sc, $^{177}$Lu, $^{212}$Pb.

DETAILED DESCRIPTION OF THE INVENTION

In a first aspect, the invention relates to a novel compound having formula (I):

The compound of formula (I) is suitable for forming a metal complex. For instance, it can form a metal complex with an ion of a metal atom (in short "metal ion") selected from the group consisting of the metal elements having atomic number ranging between 20 and 31, 39, 42, 43, 44, 49, between 57 and 83 or with respective radioisotopes chosen among $^{43}$Sc, $^{44}$Sc, $^{44m}$Sc, $^{47}$Sc, $^{51}$Cr, $^{52}$Fe, $^{52}$Mn, $^{52m}$Mn, $^{55}$Co, $^{58}$Co, $^{60}$Cu, $^{61}$Cu, $^{62}$Cu, $^{64}$Cu, $^{67}$Cu, $^{67}$Ga, $^{68}$Ga, $^{72}$As, $^{86}$Y, $^{88}$Y, $^{90}$Y, $^{97}$Ru, $^{99m}$Tc, $^{103}$Ru, $^{105}$Rh, $^{109}$Pd, $^{111}$In, $^{111}$Ag, $^{112}$Ag, $^{117m}$Sn, $^{140}$La, $^{141}$Ce, $^{142}$Pr, $^{149}$Pm, $^{149}$Tb, $^{152}$Tb, $^{155}$Tb, $^{153}$Sm, $^{159}$Gd, $^{161}$Tb, $^{165}$Dy, $^{166}$Dy, $^{166}$Ho, $^{167}$Tm, $^{168}$Yb, $^{175}$Yb, $^{177}$Lu, $^{186}$Re, $^{188}$Re, $^{199}$Au, $^{203}$Pb, $^{212}$Pb, $^{205}$Bi, $^{206}$Bi, $^{210}$Bi, $^{211}$Bi, $^{212}$Bi, $^{213}$Bi and $^{214}$Bi.

Preferably said metal ion is an ion of a radioactive metal atom. In this description and claims, the expression radioactive metal atom(s) indicates a radioactive form of a metal element and it used interchangeably with the expressions radiometal(s) radionuclide(s), radiometallic nuclide(s) and radioisotope(s).

A further aspect of the invention relates to the use of the metal complexes of the compound of formula I as a diagnostic imaging agent (e.g. PET/SPECT imaging) or as therapeutic agent (e.g. alpha/beta/Auger), particularly for the diagnosis or treatment of neuroendocrine tumors.

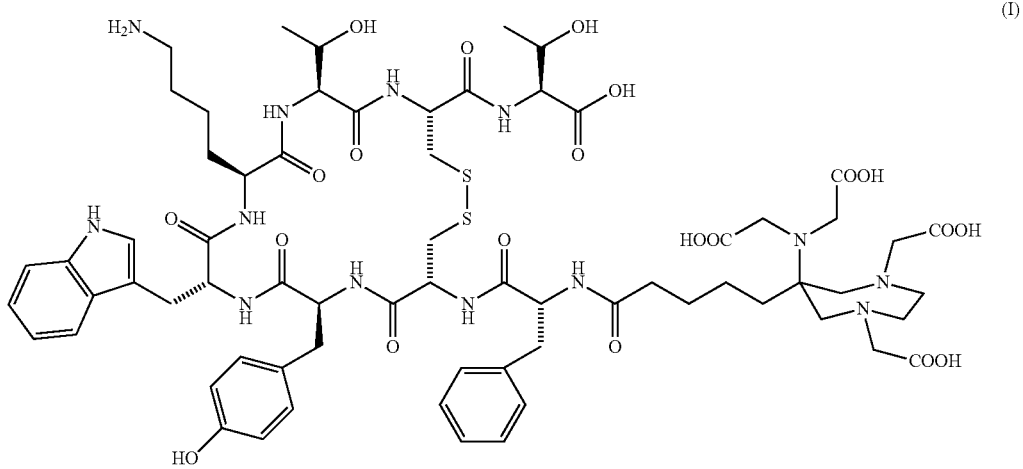

(I)

or a pharmaceutically acceptable salt thereof.

The above compound of formula (I) will be identified in the following as "AAZTA-TATE".

The preparation of AAZTA-TATE can be performed by using amide chemistry (for instance according to the detailed description in the working examples), which includes the following steps:

A. Solid phase peptide synthesis of octapeptide (TATE) (Petersen, J. Control. Release, 160, 2012, 254-263);

B. N-terminal acylation with 6-[Bis[2-(1,1-dimethylethoxy)-2-oxoethyl]amino]-6-(5-carboxypentyl)tetrahydro-1H-1,4-diazepine-1,4(5H)-Diacetic acid α,α'-bis(1,1-dimethylethyl)ester ((tBu)$_4$-AAZTA-C4-COOH);

C. Cleavage from the solid support and deprotection;

D. Purification by preparative HPLC of the final compound.

Alternatively, AAZTA-TATE may be prepared by using other chemistry routes readily available to those skilled in the art by using functionalities such as thioamide, ester, thioester, ether, thioether, urea, thiourea, triazole.

In particular, certain metal complexes of the present invention can be used as diagnostic imaging agents, preferably for in vivo diagnostic (e.g. PET/SPECT) application.

Examples of metal atoms suitable for in vivo diagnostic application are selected from the group consisting of $^{43}$Sc, $^{44m}$Sc, $^{44}$Sc, $^{52}$Fe, $^{52}$Mn, $^{52m}$Mn, $^{60}$Cu, $^{61}$Cu, $^{62}$Cu, $^{64}$Cu, $^{67}$Ga, $^{68}$Ga, $^{72}$As, $^{86}$Y, $^{99m}$Tc, $^{111}$In, $^{152}$Tb, $^{155}$Tb, $^{199}$Au and $^{203}$Pb.

In a preferred embodiment, said metal complexes for in vivo diagnostic application are used in detecting a neuroendocrine tumor.

Certain metal complexes of the present invention can be used as therapeutic agents, preferably for theranostic or radiotherapy (e.g. beta/alpha) application.

Examples of metal atoms suitable for therapeutic application are selected from the group consisting of $^{47}$Sc, $^{67}$Cu, $^{88}$Y, $^{90}$Y, $^{97}$Ru, $^{103}$Ru, $^{105}$Rh, $^{109}$Pd, $^{111}$Ag, $^{112}$Ag, $^{117m}$Sn, $^{140}$La, $^{149}$Pm, $^{149}$Tb, $^{153}$Sm, $^{161}$Tb, $^{165}$Dy, $^{166}$Dy, $^{166}$Ho, $^{167}$Tm, $^{168}$Yb, $^{175}$Yb, $^{177}$Lu, $^{186}$Re, $^{188}$Re, $^{199}$Au, $^{205}$Bi, $^{206}$Bi, $^{210}$Bi, $^{211}$Bi, $^{212}$Bi, $^{212}$Pb, $^{213}$Bi and $^{214}$Bi.

In a preferred embodiment, said metal complexes for therapeutic application are used in the treatment of a neuroendocrine tumor.

In certain embodiments of the invention, the compound of formula (I) forms metal complexes with a metal ion selected from the group of transition metals and post-transition metals, such as $^{68}$Ga. Similar metal ions are ions deriving from the nuclides $^{51}$Cr, $^{52}$Fe, $^{52}$Mn, $^{52m}$Mn, $^{55}$Co, $^{58}$Co, $^{60}$Cu, $^{61}$Cu, $^{62}$Cu, $^{64}$Cu, $^{67}$Cu, $^{67}$Ga, $^{103}$Ru, $^{105}$Rh, $^{109}$Pd, $^{111}$In, $^{186}$Re, $^{188}$Re, $^{203}$Pb, $^{212}$Pb, $^{205}$Bi, $^{206}$Bi, $^{210}$Bi, $^{211}$Bi, $^{212}$Bi, $^{213}$Bi and $^{214}$Bi. Preferably, the metal ion of the complex of the compound of formula (I) is an ion of a metal atom selected from the group consisting of Ga, Co and Cu.

In other embodiments the compound of formula (I) forms metal complexes with an ion of a metal atom selected from the group of rare earth metals, such as $^{44}$Sc. Similar metal ions are ions deriving from the nuclides $^{43}$Sc, $^{44m}$Sc, $^{47}$Sc, $^{86}$Y, $^{88}$Y, $^{90}$Y, $^{140}$La, $^{141}$Ce, $^{142}$Pr, $^{149}$Pm, $^{149}$Tb, $^{152}$Tb, $^{155}$Tb, $^{153}$Sm, $^{159}$Gd, $^{161}$Tb, $^{165}$Dy, $^{166}$Dy, $^{166}$Ho, $^{167}$Tm, $^{168}$Yb, $^{175}$Yb, $^{177}$Lu. Preferably the metal ion of the complex of the compound of formula (I) is an ion of a metal atom selected from the group consisting of Sc, Y, La, Ce, Tb, Sm, Gd, Dy, Ho, Tm, Yb and Lu.

In further embodiments the compound of formula (I) forms metal complexes with a metal ion selected from the group of soft metals, such as $^{213}$Bi. Similar metal ions are ions deriving from the nuclides $^{103}$Ru, $^{105}$Rh, $^{109}$Pd, $^{186}$Re, $^{188}$Re, $^{203}$Pb, $^{212}$Pb, $^{205}$Bi, $^{206}$Bi, $^{210}$Bi, $^{211}$Bi, $^{212}$Bi and $^{214}$Bi. Preferably the metal ion of the complex of the compound of formula (I) is an ion of Bi or Pb.

In particularly preferred embodiments, the compound of formula (I) is complexed with a metal ion selected from $^{44}$Sc, $^{47}$Sc, $^{68}$Ga, $^{177}$Lu, $^{212}$Pb or $^{213}$Bi.

The compound of formula (I) can be successfully labelled with "cold" or "hot" metals at room temperature, with yields exceeding 90% in 5 minutes. In the present description, and unless otherwise provided, the expressions "cold" or "hot" metal refer to nonradioactive and radioactive metal ions, respectively.

Advantageously, the presence of the peptide TATE linked to AAZTA does not negatively affect the labeling process. The labeling can be carried out in various buffering media including, for instance, NaOAc, NH$_4$OAc or HEPES buffers of various molarity and pH. The reaction temperature could be anywhere between room temperature (20° C.) to 95° C., preferably between 20° C. and 50° C. The timing could be anywhere between 1-60 minutes, preferably between 5 and 15 minutes.

The labelled compounds are stable in human plasma and DTPA solutions for few hours. For instance, $^{68}$GaAAZTA-TATE is stable at pH 4 and 7.4 for two hours in DTPA solution (≥98% radiochemical purity (RCP)), while $^{44}$ScAAZTA-TATE is stable (≥95% RCP) until 24 hours at both pH values.

Advantageously, high quantitative radiochemical yield (RCY) can be achieved with the compound of formula (I) by using a relatively low amount of ligand. A lower amount of ligand for complete radiochelation results in tracer with higher radiospecific activity. This may lead to higher tumor uptake resulting in superior imaging (more accurate quantification of receptor density at tumor sites and in addition it is also possible to identify tumors which express very low receptor density) and therapy.

The complexes of the compound of formula (I) further show remarkably enhanced cell internalization in comparison with respective complexes with DOTA-TATE, as illustrated in detail in the in vitro examples.

Surprisingly, as illustrated in detail in the examples, the Applicant has found that the metal complexes of AAZTA-TATE displayed unexpectedly improved in vivo properties with respect to complexes of DOTA-TATE with the same metal. For instance, metal complexes of AAZTA-TATE displayed better in vivo accumulation and better in vivo imaging when compared with the metal complexes of DOTA-TATE.

Furthermore, as illustrated in detail in the examples, the Applicant has found that the complexes of AAZTA-TATE displayed an unexpected higher kinetic inertness than the parent complexes.

In the present description, given a metal complex of the compound of formula (I), wherein the ligand is the bioconjugate AAZTA-TATE and the metal ion is M, the expression "parent complex(es)" indicates the corresponding non-targeted metal complex(es), wherein the ligand is AAZTA not conjugated with the targeting molecule TATE, and the metal ion is M.

The comparison of the dissociation half-life values ($t_{1/2}$=ln 2/$k_d$, $k_d$ is the pseudo-first order rate constant characterizing the dissociation of the complex) shows that the kinetic inertness of the AAZTA-TATE complexes is higher than the corresponding non-targeted AAZTA metal complexes.

Accordingly, an embodiment of the present invention relates to a metal complex of the compound of formula (I) characterized by a kinetic inertness of at least 2 times higher with respect to the corresponding non-targeted metal complex of AAZTA.

A preferred embodiment of the present invention relates to a metal complex of the compound of formula (I) characterized by a kinetic inertness of at least four times, preferably more than five time higher with respect to the corresponding non-targeted metal complex of AAZTA.

In general, a high kinetic inertness indicates a low rate of dissociation in vivo, resulting in lower risks associated to the products of the dissociation reactions, such as free metals ions and free ligands.

In some embodiments, the metal complexes of AAZTA-TATE of the invention surprisingly display a higher conditional stability constant (pH=7.4, [Na$^+$]=0.15 M, 25° C.) with respect to the one of the corresponding parent complexes of AAZTA, in general at least twice higher than that of the corresponding complexes of AAZTA.

For instance, the complexes Ga(AAZTA-TATE) and Bi(AAZTA-TATE) display a relevant increase of the thermodynamic properties in comparison with the respective parent complexes of AAZTA.

Radiopharmaceutical metal complexes with AAZTA-TATE can be prepared using a kit for radio-labelling, comprising a vial containing the ligand (e.g. in lyophilized form, optionally in admixture with suitable additives or excipients). The radionuclide can be eluted from a radionuclide generator (e.g. in the form of a chromatographic column, on which the radionuclide and a respective parent radiometallic nuclide are adsorbed) directly into the vial containing the ligand, with the eluting solvent. The vial may be a single dose vial or a multiple dose vial, the content of which is then split in different syringes.

In a further embodiment, the invention relates to a pharmaceutical composition comprising the chelating compound of formula I or a pharmaceutical acceptable salt thereof, in admixture with a pharmaceutically acceptable excipient.

In another aspect, the invention relates to a radiopharmaceutical composition comprising an effective amount of a metal complex of a compound of formula (I) or a pharmaceutical acceptable salt thereof, optionally comprising one or more pharmaceutically acceptable excipients.

Details concerning dosages, dosage forms, modes of administration, pharmaceutically acceptable excipients (e.g. carriers, diluents, adjuvants) are known in the art (see e.g. Monograph from World Health Organisation: Document QAS/08.262/FINAL, "RADIOPHARMACEUTICALS Final text for addition to The International Pharmacopoeia", November 2008).

In a preferred aspect, the radiopharmaceutical composition of the metal complex of formula (I) may be administered by a conventional parenteral mode such as intravenous administration. For instance, pharmaceutical compositions according to the invention are properly formulated in isotonic sterile aqueous, optionally buffered, solutions for parenteral administration. Moreover, radiochemical stabilizers can be used for preventing radiolysis of the final product, such as singlet oxygen/radical scavengers, among which ascorbic acids, gentisic acid, salicylic acid etc.

To this extent, and unless otherwise provided, the term "effective amount" refers to any amount of a complex of the formula (I) according to the invention or pharmaceutical composition thereof, that is sufficient to fulfil its intended diagnostic or therapeutic purposes. Molar amounts of the chelating agent or complex are generally in the order of nanomoles for diagnostic and/or therapeutic applications (e.g. 1 to 500 nmol, typically 5 to 50 nmol for diagnostic and 50 to 250 nmol for beta therapeutic). In general, for diagnostic application a radioactive dose of 2-10 mCi/patient (Ci=Curie=37 Giga Becquerels—GBq) may be sufficient, for alpha therapy 0.2 to 100 mCi/patient may be sufficient while for beta therapy higher doses is required, e.g. 100-300 mCi/patient.

Both the ligand i.e. AAZTA-TATE, and its metal complexes can also be in the form of a salt, particularly carboxylic and amino groups (depending on the pH) can be salified with preferred cations or anions of a physiologically compatible base or acid.

The present invention thus also relates to the chelating compound of formula (I) and its metal complexes in the form of pharmaceutically acceptable salts.

The term "pharmaceutically acceptable salt" as used herein refers to a compound of the invention wherein at least one of the carboxylic or amino groups of the compound of formula I is present in ionic form (i.e. —COO⁻ or —NH$_3^+$, =NH$_2^+$, ≡NH$^+$) and interacts with a corresponding counterion.

Preferred pharmaceutically acceptable salts are those where the free carboxylic acid group(s) of the AAZTA ligand not involved with chelation of metals ion(s) are in the form of salt(s) with a corresponding cation. The actual number of said free carboxylic acid groups may depend for instance on the coordination number of the complexed metal ion and/or from the pH of the solution containing the compound.

Alternatively, or additionally, said "pharmaceutically acceptable salt" may include a derivative of the compounds of the invention wherein an amine group of TATE is in the form of salt(s) with a corresponding anion.

Suitable cations which can be used to prepare a salt of the complexes or the ligands of the invention may be either inorganic or organic cations, deriving from either inorganic and organic basis). Examples of cations of inorganic bases comprise, for instance, ions of alkali or alkaline-earth metals such as potassium, sodium, calcium or magnesium. Examples of cations of organic bases comprise, for instance, those of primary, secondary and tertiary amines such as, for instance, ethanolamine, diethanolamine, morpholine, glucamine, N-methylglucamine, N,N-dimethylglucamine.

Similarly, suitable anions which can be used to prepare a salt of the complexes or the ligands of the invention may be either inorganic or organic anions, deriving from either inorganic and organic acids. Examples of anions of inorganic acids comprise the ions of halo acids, for instance chlorides, bromides or iodides, as well as of other suitable ions such as sulfates or phosphates. Examples of anions of organic acids comprise those routinely used in pharmaceutical techniques for the preparation of salts of basic substances such as, for instance, acetate, succinate, citrate, fumarate, maleate or oxalate.

Examples of cations and/or anions of amino acids comprise, for instance, those of, glycine, lysine, arginine, ornithine or of aspartic and glutamic acids.

The preparation of the compounds of formula (I), hence encompassing the chelate complexes thereof, either as such or in the form of physiologically acceptable salts, represent a further object of the invention.

The metal complexes of the invention can be advantageously used as diagnostic imaging agent in PET or SPECT imaging methodologies or as a targeted therapeutic agent (alpha/beta/Auger), particularly for the identification or treatment of neuroendocrine tumors.

The following examples will help to further illustrate the invention.

EXAMPLES

Example 1: Synthesis of AAZTA-TATE

9-Fluorenylmethoxycarbonyl (Fmoc) amino acids and preloaded Wang Resin with H-Thr-(tBu)-OH were purchased from IRIS Biotech (Marktredwiz, Germany) and Novabiochem (Darmstad, Germany). O-(7-azabenzotriazol-1-yl)-1,1,3,3-tetra-methyluronium hexafluorophosphate (HATU), 2,4,6-colidine were purchased from Sigma Aldrich (Darmstad, Germany). All solvents were purchased by VWR International (Radnor, USA) and were used without further purifications. 6-[Bis[2-(1,1-dimethylethoxy)-2-oxoethyl] amino]-6-(5-carboxypentyl)tetrahydro-1H-1,4-diazepine-1,4(5H)-Diacetic acid α,α'-bis(1,1-dimethylethyl)ester (AAZTA-C4-COOH tetra tert butyl ester) were synthetized as reported in Manzoni et al. Chem Med Chem, 7, 2012, 1084-1093 (Supporting Information).

The immobilized linear octapeptide H-D-Phe-Cys(Acm)-Tyr(tBu)-D-Trp(Boc)-Lys(Boc)-Thr(tBu)-Cys(Acm)-Thr (tBu)-Wang Resin was synthetized automatically on Wang Resin preloaded with H-Thr(tBu)-OH (115 mg, 0.87 mmol/g) by standard Fmoc protocol. Cleavage of Fmoc group was achieved by 20% piperidine in DMF. After the linear peptide synthesis, the resin was transferred in a SPPS manual reactor and on-resin disulfide formation was achieved by addition of Tl(CF$_3$COO)$_3$ (109 mg, 0.20 mmol, 2 equiv.) in DMF (2 mL) for 75 min at room temperature. The resin was extensively washed with DMF and the N-terminal acylated with 6-[Bis[2-(1,1-dimethylethoxy)-2-oxoethyl]amino]-6-(5-carboxypentyl)tetrahydro-1H-1,4-diazepine-1,4(5H)-Diacetic acid α,α'-bis(1,1-dimethylethyl)ester ((tBu)4-AAZTA-C4-COOH) with a triple coupling with 3.1, 2 and 2 equiv. (respectively 0.31, 0.20 and 0.2 mmol; 211, 134 and 134 mg) in presence of HATU (0.31, 0.2 and 0.2 mmol) and collidine as base (6.8, 4 and 4 equiv.). The first coupling was achieved overnight at room temperature at 38 rpm. The second and the third couplings were achieved for 3 hours at room temperature at 38 rpm. After each coupling the resin was extensively washed with DMF. The peptide was cleaved from the solid support by addition of TFA/H$_2$O/TIS (95:2.5:2.5) overnight at room temperature. Final purification was achieved by preparative HPLC by employing an Atlantis prepD® C$_{18}$OBD 5 um (19×100 mm) column. Eluent: (A) 0.1% TFA in H$_2$O, (B) 0.1% TFA in CH$_3$CN. Gradient profile: isocratic at 25% of B for 8.65 min, linear gradient from 25% to 45% of B in 2.84 min, linear gradient from 45% to 100% in 1.01 min. Flow rate; 20 mL/min. AAZTA-TATE was isolated as a homogenous peak. The solvent was removed in vacuo and the product lyophilized from water to give a white solid (21 mg, yield 14%). The purity of the product was monitored by analytical HPLC using the same gradient profile and solvent mixtures as above but with Atlantis DC18 5 μm (4.6×150 mm) column. Flow rate of 1 mL/min and UV detection at 230 nm. Purity 99%. ESI-MS (m/z): calc: For C$_{67}$H$_{91}$N$_{13}$O$_{21}$S$_2$(M+2H)$^+$ 740.33 found: 740.39.

Example 2: Radiolabeling Experiments

General Conditions of Radiolabeling Experiments

Appropriate radio-HPLC methods were developed for the determination of the radiochemical yield (RCY) of the reactions. Experiments were performed at 95° C. (unless specific radiolabelling carried out at lower temperature) in closed 1.5 mL Eppendorf tubes in a heating block (My-Block, Sigma Aldrich), with a few drops of water in each cavity to facilitate uniform heating. $^{68}$Ga is eluted from an ITG $^{68}$Ge/$^{68}$Ga generator with 0.05 M hydrochloric acid. The eluate is collected in 1 mL fractions. Fraction with the highest activity (100-120 MBq each) were used for labeling, without further purification. $^{44}$Sc was obtained by the irradiation of 120-170 mg natural calcium target (Sigma Aldrich 441872, 99.99%) with 30 μA beam current on the 16 MeV Ge PETtrace 800 cyclotron for 30-60 minutes. The irradiated target material was dissolved in 3 M ultrapure hydrochloric acid, and purified on 70 mg DGA resin (Triskem DN-B25-S) then DOWEX (Sigma-Aldrich) resin according to the following protocol. The resin was filled into a 1 mL disposable SPE syringe and washed with 2 mL portions of 3 M HCl, 1 M HNO$_3$, 0.1 M HCl and 3 M HCl. The target solution was pushed through the resin, followed by 4 mL 3 M HCl to remove calcium. The resin was washed with 3 mL 3 M HCl and 3 mL 1 M HNO$_3$ in order to remove traces of iron and nickel, and eluted with 3 mL 0.1 M HCl. A 10-30 mg DOWEX resin was washed with 1 mL 3 M HCl and 5 mL H$_2$O. The first 250-300 μL of the eluate from the DGA was discarded, and the next 2.7 mL was concentrated on the DOWEX resin, washed with 1 mL H$_2$O and eluted with 8×30 μL 1 M pH=4 NH$_4$OAc buffer. The highest activity fractions are used for labeling experiments. The activity concentration was in the range of 1-3 GBq/mL. The labeling efficiency of the obtained solution was tested with AAZTA-TATE.

Radio HPLC Conditions

Applied instrument: Waters Acquity I-class UPLC liquid chromatograph (BSM, FTN, CM, PDA modules, Berthold LB513 radioactivity detector with 20 μL MX flow cell). Peak areas are decay corrected using the time of the first injection in each measurement series. RCP % values are calculated from the corrected area values.

HPLC Conditions:
Column: Kinetex XBC18 3.6 μm, 4.6×50 mm
UV-wavelength: 210; 254 nm
Column Temperature: 30° C.

Eluents for $^{68}$Ga labeling:
A: 0.1% formic acid
B: ACN:H$_2$O (9:1)
Eluents for $^{44}$Sc labeling:
A: 0.01 M oxalic acid, pH 3
B: ACN:H$_2$O (9:1)

TABLE 1

HPLC-method gradient Table

| Time (min) | Flow rate (mL/min) | A % | B % |
|---|---|---|---|
| 0 | 1.0 | 100 | 0 |
| 1 | 1.0 | 100 | 0 |
| 2.5 | 1.0 | 0 | 100 |
| 3.0 | 1.0 | 0 | 100 |
| 3.0 | 1.0 | 100 | 0 |

Labeling experiments were performed in order to determine the optimal labeling conditions for AAZTA-TATE with $^{68}$Ga and $^{44}$Sc. All samples were measured with- and without column in order to check the activity loss on the column. In those cases, where formic acid was used as eluent, the injected activity was collected and measured with a gamma counter to determine the recovery. The peak area values are decay corrected to the time of the first injection. The radiochemical purity values are calculated from the corrected values.

Labeling

During preliminary experiments, AAZTA-TATE was labeled with $^{44}$Sc in ammonium acetate and HEPES buffer at pH=4 and at pH 7 at 95° C., 5 min. HEPES buffer at pH=4 gave the best results with quantitative labeling at 0.3 μM peptide. At room temperature, AAZTA-TATE could be labeled with yields exceeding 90% in 5 minutes. For $^{68}$Ga labeling higher peptide concentration (1 μM) and longer reaction times (15-30 min) were necessary at room temperature; quantitative yield can be reach after 5 min at 95° C. using the same concentration of precursor. Based on these results pH=4 HEPES buffer at 95° C. was chosen for preparative purposes in in vitro and in vivo experiments.

Labelling with $^{44}$Sc for in vivo experiments was carried out with the aim of obtaining highest specific activity as well as quantitative RCP % for both AAZTA-TATE and DOTA-TATE. Thus, the obtained specific activity in the case of $^{44}$Sc-AAZTA-TATE labelling usually varied in the range of 85-110 GBq/μmol, whereas in the case of DOTA-TATE specific activity varied in the range of 8-20 GBq/μmol. Results demonstrate superiority of the labelling performance that can be achieved by using AAZTA-TATE instead of DOTA-TATE.

Quality Control

Scandium labeling was monitored with HPLC on Kinetex column with oxalate-acetonitrile gradient without any sign of activity loss. In our preliminary experiments, we observed the formation of a mixed complex of gallium and AAZTA with oxalate, which elutes as a broad peak with lower retention. The free $^{68}$Ga$^{3+}$ content of the product solutions or reaction mixture samples cannot be quantified without the presence of a chelating agent, because Ga$^{3+}$ is adsorbed on solid surfaces. We found, that the addition of DTPA solution (0.01 M) decreases the activity loss. The method was checked by collecting the HPLC effluent and measuring with a gamma counter.

Stability of the Labelled Compounds

The stability of the labelled compounds was determined in human plasma and DTPA solutions. $^{68}$GaAAZTA-TATE was stable at pH 4 and 7.4 for two hours in DTPA solution (98% RCP). $^{44}$ScAAZTA-TATE reached approximately 95% radiochemical purity in 24 hours at both pH values.

Plasma stability experiments were also performed in order to determine how much radiometal is released from the chelator at each time point. The labeled compounds were incubated at 37° C. in a closed syringe with human plasma for two hours in the case of $^{68}$Ga and for 24 hours in the case of $^{44}$Sc. Free $Ga^{3+}$ is adsorbed on plasma proteins, which have to be removed from the sample prior to HPLC analysis causing loss of $^{68}Ga^{3+}$. Washing of the plasma precipitate was not effective, thus DTPA was added to the plasma samples before protein precipitation in order to stabilize $Ga^{3+}$ in solution. At each time point a 50-µL sample was taken and mixed with 50 µL 10 mM pH=4 DTPA solution and left to stand for 10 minutes at 37° C. The sample was mixed with 25 µL cold 50% ethanol. 75 µL cold acetonitrile was added and the sample was centrifuged at 9000 RPM for 10 minutes. A 50-µL sample was taken from the supernatant and injected to the HPLC.

Plasma stability of both radiolabeled compounds are shown in Table 2.

TABLE 2

Plasma stability of $^{44}$Sc/$^{68}$Ga-AAZTA-TATE at 37° C.

| $^{68}$Ga-AAZTA-TATE | | $^{44}$Sc-AAZTA-TATE | |
|---|---|---|---|
| Time (min) | RCP % | Time (min) | RCP % |
| 0 | 99.99 | 0 | 99.88 |
| 10 | 99.16 | 10 min | 99.88 |
| 30 | 98.30 | 2 h | 99.88 |
| 60 | 97.34 | 20 h | 97.41 |
| 120 | 94.45 | 24 h | 96.41 |

Results demonstrate that $^{68}$GaAAZTA-TATE showed high RCP % (approximately 95% after 2 h of plasma incubation). Whereas, in the case of $^{44}$ScAAZTA-TATE, results demonstrate that RCP % is approximately 96% after 24 hours of incubation.

In conclusion, the results show that the compounds of the present invention are characterized by a high quantitative RCP after the radiolabeling procedure, being stable over time in plasma.

Example 3: In Vitro Cells Studies

Cell Lines

AR42J ((ATCC® CRL-1492™) somatostatine receptor positive rat pancreatic exocrine tumor) and human A2780 (receptor negative human ovary carcinoma) cell lines were purchased from the American Type Culture Collection (ATCC). LNCaP cells were cultured in RPMI-1640 Medium (GIBCO Life Technologies) supplemented with 10% Fetal Bovine Serum (FBS, GIBCO Life technologies) and 1% Antibiotic and Antimicotic solution (Sigma-Aldrich). A2780 cells were cultured in Dulbecco's Modified Eagle's medium (DMEM, GIBCO Life Technologies) supplemented with 10% FBS and 1% Antibiotic and Antimicotic solution. All cell lines were cultured at 5% $CO_2$, 37° C. For in vitro studies cells were used at 85% confluence and the viability of the cells was always higher than 95%, as assessed by the trypan blue exclusion test.

Cellular Uptake Studies

AR42J and A2780 cells were trypsinized centrifuged and resuspended in DMEM and were aliquoted in test tubes at a cell concentration of $1\times10^6$ mL$^{-1}$. Tubes were incubated for 15, 30, 60 and 90 min in the presence of 0.37 MBq of $^{68}$Ga- or $^{44}$Sc-labeled DOTA- or AAZTA-TATE at 37° C. After the incubation, time samples were washed three times with ice-cold PBS and the radioactivity was measured with a calibrated gamma counter (Perkin Elmer Wizard gamma counter) for 1 min within the $^{68}$Ga-sensitive energy window. Decay-corrected radiotracer uptake was expressed as counts/(min*($10^6$ cells)) (cpm). The uptake was expressed as percentage of the total radioactivity of radiotracers added to the cells (% ID/$10^6$ cells). Each experiment was performed in triplicate and the displayed data represents the mean of at least three independent experiments (±SD).

In Vitro Saturation Binding Studies

For in vitro saturation binding studies melanotic AR42J cells were used. The cells were cultured in 24-well plates ($5\times10^4$ per well) for 24 h. Different concentrations of $^{44}$Sc- or $^{68}$Ga-AAZTA-TATE were added in cell culture medium (DMEM) to each well in 200 µL volume. After 30, 90 min incubation time (in $CO_2$ incubator at 37° C.) the medium was removed and the cells were washed twice with PBS, then washed twice with glycine (0.2 M) and lysed with NaOH (1 M) for 10 min at 37° C.

Two different in vitro cells studies were carried out in order to measure ligand-receptor interactions: internalization and saturation binding.

3a. Cellular Uptake Studies of $^{44}$Sc-AAZTA-TATE vs $^{44}$Sc-DOTA-TATE

Internalization studies measure receptor-mediated radioligand uptake into cells. For this purpose, AR42J and A2780 cells were trypsinized centrifuged and resuspended in DMEM and were aliquoted in test tubes at a cell concentration of $1\times10^6$ mL$^{-1}$. Tubes were incubated for 15, 30, 60 and 90 min in the presence of 0.37 MBq of $^{44}$Sc-labeled DOTA- or AAZTA-TATE at 37° C. After the incubation time, samples were washed three times with ice-cold PBS and the radioactivity was measured with a calibrated gamma counter (Perkin Elmer Wizard gamma counter). Decay-corrected radiotracer uptake was expressed as counts/(min*($10^6$ cells)) (cpm). The uptake was expressed as percentage of the total radioactivity of radiotracers added to the cells (% ID/$10^6$ cells). Each experiment was performed in triplicate and the displayed data represents the mean of at least three independent experiments (±SD). Results are reported as ratio between the uptake of the analyzed tracer ($^{44}$Sc-AAZTA-TATE or $^{44}$Sc-DOTA-TATE expressed as percentage of the total radioactivity of the radiotracers added to the cells, % ID/$10^6$ cells) on AR42J and control cell line A2780.

Results reported in Table 3 showed a remarkable enhanced internalization of the complex $^{44}$Sc-AAZTA-TATE in comparison with $^{44}$Sc-DOTA-TATE.

TABLE 3

| | AR42J/A2780 uptake for 44Sc-AAZTA-TATE | | AR42J/A2780 uptake for 44Sc-DOTA-TATE | |
|---|---|---|---|---|
| time | Average | ±SD | Average | ±SD |
| 15 | 851 | 425 | 380 | 86 |
| 30 | 763 | 313 | 280 | 90 |
| 60 | 715 | 147 | 240 | 86 |
| 90 | 615 | 280 | 162 | 53 |

3b. In Vitro Saturation Binding Studies

The in vitro saturation binding studies measure the specific receptor-mediated uptake of a radiolabeled ligand at equilibrium with increasing radioligand concentration.

For in vitro saturation binding studies melanotic AR42J cells were used. The cells were cultured in 24-well plates ($5\times10^4$ per well) for 24 h. Different concentrations of $^{44}$Sc-AAZTA-TATE and $^{44}$Sc-DOTA-TATE were added in cell culture medium (DMEM) to each well in 200 μL volume. After 30, 90 m incubation time (in $CO_2$ incubator at 37° C.) the medium was removed and the cells were washed twice with PBS, then washed twice with glycine (0.2 M) and lysed with NaOH (1 M) for 10 min at 37° C.

Saturation curves were generated plotting the specific binding versus the concentration of radioligands. Both ligands showed good internalization, in particular the saturation curve of the complex $^{44}$Sc-AAZTA-TATE reaches a plateau at higher amount of bound specie (Table 4a and Table 4b).

TABLE 4a

44SC-AAZTA-TATE

| Conc. (pmol/mL) added in the cell culture | Bound (pmol/$10^6$ cell) at 30 min | Bound (pmol/$10^6$ cell) at 90 min |
|---|---|---|
| 0.4827 | 0.043 | 0.08 |
| 1.7174 | 0.192 | 0.349 |
| 3.7179 | 0.347 | 0.594 |
| 6.0298 | 0.656 | 0.91 |
| 14.8129 | 0.931 | 1.301 |

TABLE 4b

44SC-DOTA-TATE

| Conc. (pmol/mL) added in the cell culture | Bound (pmol/$10^6$ cell) at 30 min | Bound (pmol/$10^6$ cell) at 90 min |
|---|---|---|
| 0.795 | 0.043 | 0.132 |
| 1.803 | NA | 0.347 |
| 4.287 | 0.394 | 0.477 |
| 7.538 | 0.446 | 0.532 |
| 16.658 | 0.474 | 0.542 |

Example 4: In Vivo Imaging Results

In Vivo Uptake on AR42J (PET/MRI Imaging)

In vivo experiments were carried out 12±1 days after subcutaneous injection of tumor cells at the tumor volume of 125±10 $mm^3$. For in vivo imaging studies AR42J pancreatic tumor-bearing male CB17 SCID mice (n=5) were injected intravenously with $^{44}$Sc- or $^{68}$Ga-AAZTA-TATE (range of injected activity: 14-22 MBq) or $^{44}$Sc-DOTA-TATE via the lateral tail vein (range of injected activity: 17-22 MBq). Blocking experiment was performed injecting an excess of AAZTA-TATE before the injection of $^{44}$Sc-AAZTA-TATE (n=3). In vivo dynamic scans (0-90 min), then 20 min static scans at 2.5 h were performed. Mice were anaesthetized by 3-1.5% isoflurane (Forane) with a dedicated small animal anesthesia device during the imaging studies. For the determination of the anatomical localization of the organs and tissues, whole body T1-weighted MRI scans were performed (3D GRE EXT multi-FOV; TR/TE 15/2 ms; Phase: 100; FOV 55 mm; NEX: 2) using the preclinical nanoScan-PET/MRI system (Mediso Ltd., Hungary). PET volumes were reconstructed using the three-dimensional Ordered Subsets Expectation Maximization (3DOSEM) algorithm (Tera-Tomo, Mediso Ltd., Hungary). PET and MRI images were automatically co-registered by the acquisition software (Nucline) of nanoScan PET/MRI instrument. Reconstructed images were analyzed using the InterView™ FUSION (Mediso Ltd., Hungary) image analysis software. Ellipsoidal 3-dimensional Volumes of Interest (VOI) was manually drawn around the edge of the tissue or organ activity by visual inspection. Radiotracer uptake was expressed in terms of standardized uptake values (SUVs). SUV was calculated as follows: SUV=[VOI activity (Bq/ml)]/[injected activity (Bq)/animal weight (g)], assuming a density of 1 g/mL.

SUV mean values for in vivo PET-MRI uptake studies using tumor-bearing animals (n=5/group, n=3/blocking experiment) at 2.5 h post injection are reported in Table 5.

TABLE 5

| | $^{68}$Ga-AAZTA-TATE | | $^{44}$Sc-DOTA-TATE | | $^{44}$Sc-AAZTA-TATE | | $^{44}$Sc-AAZTA-TATE (blocked) | |
|---|---|---|---|---|---|---|---|---|
| | SUVmean | ±SD | SUVmean | ±SD | SUVmean | ±SD | SUVmean | ±SD |
| Tumor | 1.79 | 0.50 | 1.01 | 0.47 | 2.74 | 0.95 | 0.34 | 0.18 |

$^{44}$ScAAZTA-TATE in vivo results demonstrate high uptake of this compound on tumor tissues. Actually, SUV mean value (2.74 ± 0.95) results remarkably higher that $^{44}$ScDOTA-TATE SUV mean value (1.01 ± 0.47). Moreover, the blocking experiments with AAZTA-TATE demonstrated that the tumor-uptake and the accumulation of $^{44}$Sc AAZTA-TATE in sst receptor-expressing tumor is highly specific.

In conclusion, the results showed that the compounds of the present invention are characterized by a higher uptake on tumor tissues, than the corresponding compounds of DOTA. Moreover, the blocking experiments confirmed the that the tumor-uptake of the compound of the invention is highly specific.

Example 5: Stability and Kinetic Inertness Evaluation of the Compound Ga-AAZTA-TATE 5a. Equilibrium Studies of the Ga-AAZTA-TATE) Complex The thermodynamic properties of Ga-AAZTA-TATE complex was characterized by the conditional stability constant (log $K^{cond}$=log $K^{therm}/(1+\alpha_H)$ where $\alpha_H=K_1^H[H^+]+K_1^H K_2^H [H^+]^2+\ldots+K_1^H K_2^H \ldots K_n^H[H^+]^n$ and $K_1^H, K_2^H, \ldots K_n^H$ are the protonation constant of the free ligand at pH=7.0 in 0.15 M NaCl solution. Based on the equilibrium properties of Ga(AAZTA) complex, Ga(AAZTA)OH species predominates at physiological condition (Eq. (1), Baranyai, Eur. J. Inorg. Chem., 2013, 147-162). The conditional stability constant of Ga(AAZTA)OH species can be expressed by (log $K^{cond}$=log $K^{therm}/([OH^-](1+\alpha_H))$. According to the similarities, it can be assumed that Ga(AAZTA-TATE)OH complex also predominates at physiological condition.

$$Ga^{3+} + L + OH^- \rightleftharpoons Ga(L)OH \quad (1)$$

$$K_{Ga(L)OH} = \frac{[Ga(L)OH]}{[Ga^{3+}][L][OH^-]}$$

where L=AAZTA, AAZTA-TATE

The conditional stability constant of Ga(AAZTA-TATE)OH complex were determined by Capillary Zone Electrophoresis (Hewlett-Packard HP$^{3D}$ capillary electrophoresis system) studying the competition reaction of AAZTA-TATE with AAZTA for Ga$^{3+}$ at pH=7.0 and 25° C. in 0.15 M NaCl solution, as it is disclosed in Chang, J. Chinese. Chem. Soc. 1999, 46, 519-528. In these experiments, the concentration of Ga$^{3+}$ and AAZTA-TATE was 25.0 μM, while that of the AAZTA was varied between 25.0 and 150.0 μM (6×1 mL samples). The pH was adjusted to pH=7.0 by stepwise addition of concentrated NaOH or HCl. The samples were kept at 50° C. for 3 days and then at 25° C. for two weeks in order to attain the equilibrium (the time needed to reach the equilibria was determined by capillary electrophoresis). The amount of the Ga(AAZTA-TATE)OH complex decreases, whereas the free [AAZTA-TATE] increases with the increase of the [H$_x$AAZTA] according to the competition reaction between AAZTA-TATE and AAZTA for Ga$^{3+}$-ion (Eq. (2))

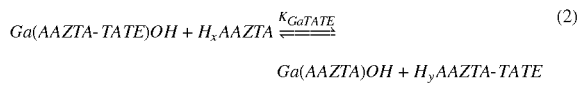

$$Ga(AAZTA\text{-}TATE)OH + H_xAAZTA \xrightleftharpoons{K_{GaTATE}} Ga(AAZTA)OH + H_yAAZTA\text{-}TATE \quad (2)$$

$$K_{GaTATE} = \frac{[Ga(AAZTA)OH][H_x(AAZTA-TATE)]}{[Ga(AAZTA-TATE)OH][H_xAAZTA]} =$$

$$\frac{K^{therm}_{Ga(AAZTA)OH}(1+\alpha_H^{AAZTA-TATE})}{K^{therm}_{Ga(AAZTA-TATE)OH}(1+\alpha_H^{AAZTA})} = \frac{K^{cond}_{Ga(AAZTA)OH}}{K^{cond}_{Ga(AAZTA-TATE)OH}}$$

where x=1 and 2. By taking into account the total concentration of AAZTA ([AAZTA]$_{tot}$=[H$_x$AAZTA]+[Ga(AAZTA)OH]) the K$_{GaTATE}$ value was calculated 0.49 (6) from the data of the Capillary Zone Electrophoresis studies. By taking into account the stability constant of [Ga(AAZTA)OH] (log K$^{therm}_{Ga(AAZTA)OH}$=16.57, 0.15 M NaCl, 25° C., Baranyai, Eur. J. Inorg. Chem., 2013, 147-162), the protonation constants of AAZTA ligands (log K$_1^H$=9.98, log K$_2^H$=6.52, log K$_3^H$=3.76, log K$_4^H$=2.21, 0.15 M NaCl, 25° C. Baranyai, Eur. J. Inorg. Chem., 2013, 147-162), the conditional stability constant of Ga(AAZTA)OH was found to be log K$^{cond}_{Ga(AAZTA)OH}$=20.1 at pH=7.0 and 25° C. in 0.15 M NaCl solution. By taking into account the K$_{GaTATE}$ equilibrium constant (K$_{GaTATE}$=0.49) and the conditional stability constant of Ga(AAZTA)OH (log K$^{cond}_{Ga(AAZTA)OH}$=20.1), the conditional stability constant of Ga(AAZTA-TATE)OH complex (log K$^{cond}_{Ga(AAZTA-TATE)OH}$=log K$^{cond}_{Ga(AAZTA)OH}$−log K$_{GaTATE}$) was found to be log K$^{cond}_{Ga(AAZTA-TATE)OH}$=20.5. Based on these evidence, the conditional stability constant of Ga(AAZTA-TATE)OH complex is higher by about 0.4 log K unit than that of the Ga(AAZTA)OH complex.

5b. Kinetic Studies of the Transchelation Reaction of Ga(AAZTA-TATE)OH Complex with Human Serum Transferrin The ligand exchange reaction of Ga(AAZTA-TATE)OH and the human serum apo-transferrin (sTf, Sigma) have been studied by spectrophotometry (Eq. (3)), following the formation of Ga-transferrin complex at 246 nm and pH=7.4 with the use of a Agilent 8453 UV-Vis spectrophotometer using 1.0 cm cells in the presence of Ga(AAZTA-TATE)OH excess to guarantee the pseudo-first-order kinetic condition as it is disclosed in Baranyai, Eur. J. Inorg. Chem., 2013, 147-162) ([Ga(AAZTA-TATE)OH]=50 μM, [Trf]=8 and 16 μM). The concentration of the human serum transferrin solution was determined from the absorbance at 280 nm using the molar absorptivity $\varepsilon_{280}$=91200 cm$^{-1}$M$^{-1}$ (Takahashi, J. Biochem. 1989, 106, 858-863). The temperature was maintained at 25° C., the ionic strength and the hydrogen-carbonate concentration of the samples was kept constant; 0.15 M for NaCl and 0.025 M for NaHCO$_3$, respectively.

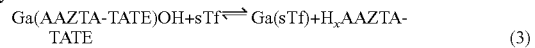

$$Ga(AAZTA\text{-}TATE)OH + sTf \rightleftharpoons Ga(sTf) + H_xAAZTA\text{-}TATE \quad (3)$$

The rate of the transchelation reactions between Ga(AAZTA-TATE)OH and sTf obtained at [Ga(AAZTA-TATE)OH]=50 μM and [sTf]=8 and 16 μM are 7.86×10$^{-11}$ and 8.17×10$^{-11}$ mol/dm$^{-3}$s$^{-1}$, respectively. These kinetic data clearly indicates that the [sTf] has practically no effect for the dissociation rate of Ga(AAZTA-TATE)OH. By taking into account the rate of reactions (d[Ga(sTf)]/dt=k$_d$[Ga(AAZTA-TATE)]$_t$=7.86×10$^{-11}$ and 8.17×10$^{-11}$ mol/dm$^{-3}$s$^{-1}$), the k$_d$ pseudo-first-order rate constants characterizing the transchelation reactions between Ga(AAZTA-TATE)OH and sTf have been calculated. The k$_d$ pseudo-first-order rate constants and half-life values (t$_{1/2}$=ln 2/k$_d$) of the transchelation reactions between Ga(AAZTA-TATE)OH and sTf are summarized and compared with those of the ligand exchange reactions between [Ga(AAZTA)OH] and sTf in Table 6.

TABLE 6

Rate constants (k$_d$) and half-time (t$_{1/2}$ = ln2/k$_d$) of of the transchelation reactions between Ga(AAZTA-TATE)OH and sTf, Ga(AAZTA)OH and sTf near to physiological conditions (pH = 7.4, 0.025M NaHCO$_3$, 0.15M NaCl, 25° C.)

|  | Ga(AAZTA-TATE)OH - sTf | Ga(AAZTA)OH - sTf[a] |
|---|---|---|
| k$_d$ (s$^{-1}$) | 1.60 × 10$^{-6}$ | 8.0 × 10$^{-6}$ |
| t$_{1/2}$ (hours) at pH = 7.4 | 121 | 24 |

[a]Ref. [Baranyai, Eur. J. Inorg. Chem., 2013, 147-162]

The average value of the k$_d$ for the transchelation reactions between Ga(AAZTA-TATE)OH and sTf was found to be 1.60×10$^{-6}$ s$^{-1}$, which is about 5.4 smaller than that of the transchelation reaction between Ga(AAZTA)OH and sTf (8.0×10$^{-6}$ s$^{-1}$) at close to physiological condition (pH=7.4, 0.025 M NaHCO$_3$, 0.15 M NaCl). By taking into account the k$_d$ values, the half-life of the transchelation reaction (t$_{1/2}$=ln 2/k$_d$) between Ga(AAZTA-TATE)OH and sTf is about 5.4 times longer than that of the t$_{1/2}$ values obtained in the ligand exchange reactions of Ga(AAZTA)OH with sTf.

Example 6: Stability and Kinetic Inertness Evaluation of Sc(AAZTA-TATE)

6a. Equilibrium Studies

The thermodynamic properties of Sc(AAZTA-TATE) complex were characterized by the conditional stability constant (log K$^{cond}$=log K$^{therm}$/(1+α$_H$) where α$_H$=K$_1^H$[H$^+$]+

$K_1^H K_2^H [H^+]^2 + \ldots + K_1^H K_2^H \ldots K_n^H [H^+]^n$ and $K_1^H$, $K_2^H, \ldots K_n^H$ are the protonation constant of the free ligand) at pH=7.4 in 0.15 M NaCl solution. To determine the log $K^{cond}$ value of Sc(AAZTA-TATE) complex, the competition reaction of AAZTA-TATE with NTA for $Sc^{3+}$ have been studied by $^{45}Sc$ NMR spectroscopy (Bruker Avance III 400 spectrometer at 9.4 T) with the integral of $Sc(NTA)_2$ complex ($\delta_{Sc}$=59.9 ppm) formed in the reactions (Eq. (4), $H_3NTA$=nitrilo-triacetic acid, pH=7.4, 25° C., 0.15 M NaCl).

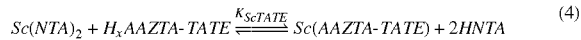

$$Sc(NTA)_2 + H_xAAZTA\text{-}TATE \underset{}{\overset{K_{ScTATE}}{\rightleftharpoons}} Sc(AAZTA\text{-}TATE) + 2HNTA \quad (4)$$

For the equilibrium characterization of Sc(AAZTA-TATE), 7 samples were prepared in which the concentration of $Sc^{3+}$ and AAZTA-TATE was 203.3 μM and 206.2 μM, while that of the NTA was varied between 0.0 and 20.06 mM (7×1 mL samples were prepared by the addition of AAZTA-TATE to the pre-prepared $Sc(NTA)_2$ complex) in 0.15 M NaCl solution. The pH was adjusted to pH=7.4 by stepwise addition of concentrated NaOH or HCl solutions. The samples were kept at 25° C. for 8 weeks in order to attain the equilibrium (the time needed to reach the equilibria was determined by $^{45}Sc$ NMR spectroscopy).

To compare the equilibrium properties of Sc(AAZTA-TATE) with that of Sc(AAZTA), the conditional stability constant of Sc(AAZTA) was determined by following the competition reaction of AAZTA with NTA for $Sc^{3+}$ with $^{45}Sc$ NMR spectroscopy by using the integral of $Sc(NTA)_2$ complex ($\delta_{Sc}$=59.9 ppm) formed in the reactions (Eq. (5), pH=7.4, 25° C., 0.15 M NaCl).

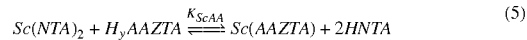

$$Sc(NTA)_2 + H_yAAZTA \underset{}{\overset{K_{ScAA}}{\rightleftharpoons}} Sc(AAZTA) + 2HNTA \quad (5)$$

For the equilibrium characterization of Sc(AAZTA), 7 samples were prepared in which the concentration of $Sc^{3+}$ and AAZTA was 203.3 μM and 207.1 μM, while that of the NTA was varied between 0 and 20.06 mM (7×2 mL samples with the addition of AAZTA to the pre-prepared $Bi(NTA)_2$ complex) in 0.15 M NaCl solution. The pH was adjusted to pH=7.4 by stepwise addition of concentrated NaOH or HCl solutions. The samples were kept at 25° C. for 8 weeks in order to attain the equilibrium (the time needed to reach the equilibria was determined by $^{45}Sc$ NMR spectroscopy). For the equilibrium calculation, the protonation constants of NTA ligand (NTA: log $K_1^H$=9.13 (1), log $K_2^H$=2.63 (2), log $K_3^H$=1.64 (3); 25° C., 0.15 M NaCl) and the stability constants of Sc(NTA) and $Sc(NTA)_2$ complexes (log $K_{Sc(NTA)}$=14.12 (3), log $\beta_{Sc(NTA)2}$=24.08 (2), 25° C., 0.15 M NaCl) have been determined by pH-potentiometry and $^{45}Sc$ NMR spectroscopy, as it is described in the literature (Nagy, Angew Chem Int Ed Engl 2017, 56, 2118-2122).

The amount of the $Sc(NTA)_2$ complex increases with the increase of [NTA] according to the competition reactions of AAZTA-TATE and AAZTA with NTA for $Sc^{3+}$-ion (Eqs. (4) and (5)). The competition reactions of AAZTA-TATE and AAZTA with NTA for $Sc^{3+}$-ion (Eqs. (4) and (5)) can be characterized by $K_{ScTATE}$ and $K_{ScAA}$ equilibrium constants which can be expressed by the following equations:

$$K_{ScTATE} = \frac{[Sc(AAZTA-TATE)][H_yNTA]^2}{[Sc(NTA)_2][AAZTA-TATE]] = \quad (6)$$

$$\frac{K_{Sc(AAZTA-TATE)}(1+\alpha_H^{NTA})^2}{K_{Sc(NTA)2}(1+\alpha_H^{AAZTA-TATE})} = \frac{K^{cond}_{Sc(AAZTA-TATE)}}{K^{cond}_{Sc(NTA)2}}$$

$$K_{ScAA} = \quad (7)$$

$$\frac{[Sc(AAZTA)][H_yNTA]^2}{[Sc(NTA)_2][AAZTA]} = \frac{K_{Sc(AAZTA)}(1+\alpha_H^{NTA})^2}{K_{Sc(NTA)2}(1+\alpha_H^{AAZTA})} = \frac{K^{cond}_{Sc(AAZTA)}}{K^{cond}_{Sc(NTA)2}}$$

By taking into account the total concentration of NTA ([NTA]$_{tot}$=[H$_x$NTA]+2[Sc(NTA)$_2$]), $Sc^{3+}$ ion ([$Sc^{3+}$]$_{tot}$=[Sc(NTA)$_2$]+[Sc(AAZTA-TATE)]) and AAZTA-TATE ([AAZTA-TATE]$_{tot}$=[Sc(AAZTA-TATE)]+[H$_x$AAZTA-TATE]), the value of $K_{ScTATE}$ (Eq. (6)) was calculated from integral value of $Sc(NTA)_2$ complex in $^{45}Sc$ NMR spectra of $Sc^{3+}$-AAZTA-TATE-NTA systems ($K_{ScTATE}$=3.42 (9)). Considering the stability constant of $Sc(NTA)_2$ predominates at our experimental condition (log $\beta_{Sc(NTA)2}$=24.08, 0.15 M NaCl, 25° C.) and the protonation constants of NTA ligands (log $K_1^H$=9.13 (1), log $K_2^H$=2.63 (2), log $K_3^H$=1.64 (3); 25° C., 0.15 M NaCl), the conditional stability constant of $Sc(NTA)_2$ was found to be log $K^{cond}_{Sc(NTA)2}$=20.63 at pH=7.4 and 25° C. in 0.15 M NaCl solution. By taking into account the $K_{ScTATE}$ equilibrium constant ($K_{ScTATE}$=3.42) and the conditional stability constant of $Sc(NTA)_2$ (log $K^{cond}_{Sc(NTA)2}$=20.63), the conditional stability constant of Sc(AAZTA-TATE) complex (log $K^{cond}_{Sc(AAZTA-TATE)}$=log $K_{ScTATE}$+log $K^{cond}_{Sc(NTA)2}$) was found to be log $K^{cond}_{Sc(AAZTA-TATE)}$=21.2 at pH=7.4 and 25° C. in 0.15 M NaCl.

By taking into account the total concentration of NTA ([NTA]$_{tot}$=[H$_x$NTA]+2[Sc(NTA)$_2$]), $Sc^{3+}$ ion ([$Sc^{3+}$]$_{tot}$=[Sc(NTA)$_2$]+[Sc(AAZTA)] and AAZTA ([AAZTA]$_{tot}$=[Sc(AAZTA)]+[H$_x$AAZTA]) the value of $K_{ScAA}$ (Eq. (7)) was calculated from integral value of $Sc(NTA)_2$ complex in $^{45}Sc$ NMR spectra of $Sc^{3+}$-AAZTA-NTA systems ($K_{ScAA}$=70.3 (5)). Considering the $K_{ScAA}$ equilibrium constant ($K_{ScAA}$=70.3) and the conditional stability constant of $Sc(NTA)_2$ (log $K^{cond}_{Sc(NTA)2}$=20.63), the conditional stability constant of Sc(AAZTA) complex (log $K^{cond}_{Sc(AAZTA)}$= log $K_{ScAA}$+log $K^{cond}_{Sc(NTA)2}$) was calculated to be log $K^{cond}_{Sc(AAZTA)}$=22.5 at pH=7.4 and 25° C. in 0.15 M NaCl. Based on these evidence, the conditional stability constant of Sc(AAZTA-TATE) complex is lower by about 1 log K unit than that of the Sc(AAZTA) complex at pH=7.4 and 25° C. in 0.15 M NaCl.

6b. Kinetic Studies of the Transchelation Reaction Between Sc(AAZTA-TATE) and NTA Ligand (NTA=Nitrilotriacetic Acid)

The ligand exchange reaction of Sc(AAZTA-TATE) with NTA (Sigma) have been studied by $^{45}Sc$ NMR spectroscopy at pH=5.5 and 25° C. The transchelation of the Sc(AAZTA-TATE) were monitored by following the integral of $Sc(NTA)_2$ complex formed in the reactions (Eq. (8)) as described above.

ScAAZTA-TATE)+2NTA $\rightleftharpoons$ Sc(NTA)$_2$+H$_x$AAZTA-TATE   (8)

For the kinetic experiments, two samples were prepared in which the concentration of Sc(AAZTA-TATE) was 0.2 mM in the presence of 2500 and 5000 fold excess of NTA ligand in order to guarantee the pseudo-first-order kinetic condition (2×0.8 mL samples). The pH was adjusted to pH=5.5 by stepwise addition of concentrated NaOH or HCl. For keeping the pH values constant, buffer was not used due to the presence of NTA in a high concentration. In $^{45}Sc$ NMR spectra of the Sc(AAZTA-TATE)-NTA reacting system, the transchelation reaction of Sc(AAZTA-TATE) with NTA results in the increase of the integral of Sc(NTA)$_2$ complex according to Eq. (8). The pseudo-first-order rate constants (k$_d$) were calculated by fitting of the integral (Sc(NTA)$_2$)—time data sets to Eq. (9).

$$A_t = A_e + (A_0 - A_e)e^{-k_d t} \quad (9)$$

where A$_t$, A$_0$ and A$_e$ are the integral values at time t, at the beginning and at the end of the reactions, respectively.

Based on the similarities, it can be assumed that the mechanism of the tranchelation reaction of Sc(AAZTA-TATE) is very similar to that of the parent Sc(AAZTA) complex. (Nagy, Angew Chem Int Ed Engl 2017, 56, 2118-2122). Transchelation reaction of Sc(AAZTA-TATE) occurs by the rate determining H$^+$ assisted dissociation of Sc(AAZTA-TATE) complex which has been followed by the fast reaction between the free Sc$^{3+}$ and the exchanging NTA ligand. The pseudo-first-order rate constant (k$_d$) characterizing the transchelation reactions between Sc(AAZTA-TATE) and NTA obtained at [Sc(AAZTA-TATE)]=0.2 mM and [NTA]=0.5 and 1.0 M and pH=5.50 and 5.35 are (1.7±0.2)×10$^{-7}$ s$^{-1}$ and (1.8±0.3)×10$^{-7}$ s$^{-1}$, respectively. These kinetic data clearly indicate that the [NTA] has practically no effect for the dissociation rate of Sc(AAZTA-TATE).

The comparison of the dissociation half-life values (t$_{1/2}$=ln 2/k$_d$) of Sc(AAZTA) and Sc(AAZTA-TATE) obtained at pH=5.50 and 5.35 (Sc(AAZTA): t$_{1/2}$=469 and 600 hours Nagy, Angew Chem Int Ed Engl 2017, 56, 2118-2122; Sc(AAZTA-TATE): t$_{1/2}$=1100 and 1050 hours, 25° C.) indicates that the kinetic inertness of Sc(AAZTA-TATE) is higher by about two times than that of Sc(AAZTA).

Example 7: Stability and Kinetic Inertness Evaluation of the Compound Bi-AAZTA-TATE)

7a. Equilibrium Studies

The stability constant of Bi(AAZTA) was determined by following the competition reaction of AAZTA with NTA for Bi$^{3+}$ (Eq. (10)) with UV-spectrophotometry in the wavelength range of 210-350 nm. The concentration of Bi$^{3+}$ and NTA was 30.2 μM and 10 mM while that of the AAZTA was varied between 0 and 50 μM (6×2 mL samples with the addition of AAZTA to the pre-prepared Bi(NTA)$_2$ complex) in 0.15 M NaClO$_4$ solution. The pH was adjusted to pH=7.4 by stepwise addition of concentrated NaOH or HClO$_4$. The samples were kept at 50° C. for a week and at 25° C. for two weeks in order to attain the equilibrium (the time needed to reach the equilibria was determined by spectrophotometry). The spectrophotometric measurements were made with the use of PerkinElmer Lambda 365 UV-Vis spectrophotometer at 25° C., using 1.0 cm cells. For the equilibrium calculation, the protonation constants of AAZTA and NTA ligands (AAZTA: log K$_1^H$=10.29, log K$_2^H$=6.51, log K$_3^H$=3.86, log K$_4^H$=1.94, log K$_5^H$=1.00; NTA: log K$_1^H$=9.22, log K$_2^H$=2.98, log K$_3^H$=1.06; 25° C., 0.15 M NaClO$_4$) and the stability constants of Bi(NTA) and Bi(NTA)$_2$ complexes (log K$_{Bi(NTA)}$=16.97, log β$_{Bi(NTA)2}$=26.21, 25° C., 0.15 M NaClO$_4$) have been determined as it is described in the literature (Baranyai, Eur. J. Inorg. Chem., 2013, 147-162, KARADAKOV, Talanta, 1970, 17, 883-887). The equilibrium constants were calculated with the program PSEQUAD (L. Zekany and I. Nagypal in PSEQUAD, Vol. (Ed. D. Leggett), Springer US, 1985, pp. 291-353).

$$Bi(NTA)_2 + H_x AAZTA \rightleftharpoons Bi(AAZTA) + 2H_y NTA \quad (10)$$

Thermodynamic stability constant of Bi(AAZTA) calculated from the UV-spectrophotometric studies of Bi$^{3+}$-NTA-AAZTA systems is log K$_{Bi(AAZTA)}$=26.45 (6) at 25° C. in 0.15 M NaClO$_4$. By taking into account the protonation constant of AAZTA ligand (log K$_1^H$=10.29, log K$_2^H$=6.51, log K$_3^H$=3.86, log K$_4^H$=1.94, log K$_5^H$=1.00, 25° C., 0.15 M NaClO$_4$) and the stability constant of Bi(AAZTA) (log K$_{Bi(AAZTA)}$=26.45, 25° C. in 0.15 M NaClO$_4$), the conditional stability constant of Bi(AAZTA) was calculated to be log K$^{cond}_{Bi(AAZTA)}$=log K$_{Bi(AAZTA)}$/(1+α$_H$)=23.5 at pH=7.4 and 25° C. in 0.15 M NaClO$_4$ (α$_H$=K$_1^H$[H$^+$]+K$_1^H$K$_2^H$[H$^+$]$^2$+ . . . +K$_1^H$K$_2^H$ . . . K$_n^H$[H$^+$]$^n$ and K$_1^H$, K$_2^H$, . . . K$_n^H$ are the protonation constant of the free ligand at pH=7.4 in 0.15 M NaClO$_4$ solution).

The thermodynamic properties of Bi(AAZTA-TATE) complex were also characterized by the conditional stability constant (log K$^{cond}$=log K$^{therm}$/(1+α$_H$)). To determine the log K$^{cond}$ value of Bi(AAZTA-TATE) complex, the competition reaction of AAZTA-TATE with NTA for Bi$^{3+}$ (Eq. (11)) have been studied by Capillary Zone Electrophoresis (Hewlett-Packard HP$^{3D}$ capillary electrophoresis system) at pH=7.4 in 0.15 M NaClO$_4$ solution as it is disclosed in Chang, J. Chinese. Chem. Soc. 1999, 46, 519-528 (H$_3$NTA=nitrilo-triacetic acid). For the equilibrium characterization of Bi(AAZTA-C4-TATE), the concentration of Bi$^{3+}$ and NTA was 30.2 μM and 15.0 mM, while that of the AAZTA-C4-TATE was varied between 0.0 and 50.4 μM (5×1 mL samples with the addition of AAZTA-C4-TATE to the pre-prepared Bi(NTA)$_2$ complex) in 0.15 M NaClO$_4$ solution. The pH was adjusted to pH=7.4 by stepwise addition of concentrated NaOH or HClO$_4$. The samples were kept at 50° C. for a week and at 25° C. for two weeks in order to attain the equilibrium (the time needed to reach the equilibria was determined by capillary electrophoresis).

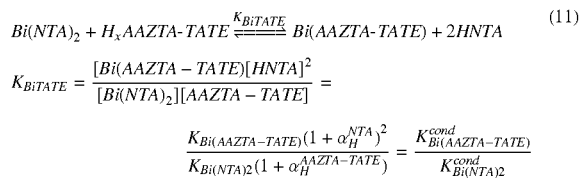

$$Bi(NTA)_2 + H_x AAZTA\text{-}TATE \xrightleftharpoons{K_{BiTATE}} Bi(AAZTA\text{-}TATE) + 2HNTA \quad (11)$$

$$K_{BiTATE} = \frac{[Bi(AAZTA-TATE)][HNTA]^2}{[Bi(NTA)_2][AAZTA-TATE]} = \frac{K_{Bi(AAZTA-TATE)}(1+\alpha_H^{NTA})^2}{K_{Bi(NTA)2}(1+\alpha_H^{AAZTA-TATE})} = \frac{K^{cond}_{Bi(AAZTA-TATE)}}{K^{cond}_{Bi(NTA)2}}$$

The amount of the Bi(AAZTA-TATE) complex increases by increasing the amount of AAZTA-TATE according to the competition reaction between AAZTA-TATE and NTA for Bi$^{3+}$-ion (Eq. (11)) By taking into account the total concentration of NTA ([NTA]$_{tot}$=[H$_x$NTA]+2[Bi(NTA)$_2$]), Bi$^{3+}$ ion ([Bi$^{3+}$]$_{tot}$=[Bi(NTA)$_2$]+[Bi(AAZTA-TATE)]) and AAZTA-TATE ([AAZTA-TATE]$_{tot}$=[Bi(AAZTA-TATE)]+[H$_x$AAZTA-TATE]) the K$_{BiTATE}$ value was found to be 51 (9). Considering the stability constant of Bi(NTA)$_2$ (log β$_{Bi(NTA)2}$=26.21, 0.15 M NaClO$_4$, 25° C.) and the protonation constants of NTA ligands log K$_1^H$=9.22, log K$_2^H$=2.98, log K$_3^H$=1.06; 25° C., 0.15 M NaClO$_4$), the conditional stability constant of Bi(NTA)$_2$ was found to be log K$^{cond}_{Bi(NTA)2}$=22.5 at pH=7.4 and 25° C. in 0.15 M NaClO$_4$ solution. By taking into account the K$_{BiTATE}$ equilibrium constant (K$_{GaTATE}$=51) and the conditional stability constant of Bi(NTA)$_2$ (log K$^{cond}_{Bi(NTA)2}$=22.5), the conditional stability constant of Bi(AAZTA-TATE) complex (log K$^{cond}_{Bi(AAZTA-TATE)}$=log K$_{BiTATE}$+log K$^{cond}_{Bi(NTA)2}$) was found to be log K$^{cond}_{Bi(AAZTA-TATE)}$=24.3 at pH=7.4 and 25° C. in 0.15 M NaClO$_4$.

Based on these evidence, the conditional stability constant of Bi(AAZTA-TATE) complex is higher by about 0.8 log K unit than that of the Bi(AAZTA) complex at pH=7.4 and 25° C. in 0.15 M NaClO$_4$.

7b. Kinetic Studies of the Transchelation Reaction Between Bi(AAZTA-TATE) and AAZTA Ligand, and Bi(AAZTA) and DTPA Ligand.

The kinertic properties of Bi(AAZTA) was determined by following the transchelation reaction between Bi(AAZTA) and DTPA with UV-spectrophotometry at 278 nm and 25° C. in 0.15 M NaClO$_4$ solution (stability constant of Bi(DTPA) is log $K_{Bi(DTPA)}$=29.3 at 25° C. in 0.6 M NaClO$_4$, V. Kornev, A. Troubachev, *Russ. J. Inorg. Chem*, 1987, 32, 1419). In these experiments the concentration of Bi(AAZTA) was 0.1 mM while DTPA was applied in 10 and 20 fold excess to ensure the occurrence of pseudo-first order conditions. The pH was adjusted to 8.5, 9.0, 9.5, 10.0, 10.5 and 11.0 by stepwise addition of concentrated NaOH or HClO$_4$. For keeping the pH values constant 0.01 M N-methyl-piperazine (pH≤10) buffers were used. At pH>10, buffer was not used to keep the constant pH due to the presence of OH$^-$ in a high concentration. The pseudo-first-order rate constants ($k_d$) were calculated by fitting the absorbance—time data sets for Bi(AAZTA)—DTPA system to Eq. (9). The dissociation rates ($k_d$) of Bi(AAZTA) complex is independent from the [DTPA] and increase with the increase of pH. The increase of $k_d$ values with increasing pH (with the increase of [OH$^-$]) can be interpreted in terms of the rate determining OH$^-$ assisted dissociation of Bi(AAZTA) complex which has been followed by the fast reaction between the free Bi$^{3+}$ and the exchanging DTPA ligand. $k_d$ rate constant and the half-life ($t_{1/2}$=ln 2/$k_d$) characterizes the dissociation reaction of Bi(AAZTA) was found to be $k_d$=1.67×10$^{-6}$ s$^{-1}$ and $t_{1/2}$=115 hours at pH=9.0 and 25° C. in 0.15 M NaClO$_4$.

In order to examine the kinetic inertness of Bi(AAZTA-TATE) complex, the transchelation reactions between Bi(AAZTA-TATE) complex and AAZTA (Eq. (12)) have been studied by Capillary Zone Electrophoresis (Hewlett-Packard HP$^{3D}$ capillary electrophoresis system) at pH=9.0 and 25° C. in 0.15 M NaClO$_4$ in the presence of 20 and 40 fold AAZTA excess to guarantee the pseudo-first-order kinetic condition.

$$\text{Bi(AAZTA-TATE)} + \text{AAZTA} \rightleftharpoons \text{Bi(AAZTA)} + \text{H}_x\text{AAZTA-TATE} \quad (12)$$

For the kinetic experiments, two samples were prepared in which the concentration of Bi(AAZTA-TATE) was 50.1 μM in the presence of 20 and 40 fold excess AAZTA ligand in order to guarantee the pseudo-first-order kinetic condition (2×1 mL samples in 0.15 M NaClO$_4$ solution). The pH was adjusted to pH=9.0 by stepwise addition of concentrated NaOH or HClO$_4$. For keeping the pH values constant 0.01 M N-methyl-piperazine (NMP) buffers were used. The samples were kept at 25° C. In the electropherograms of the Bi(AAZTA-TATE)-AAZTA reacting systems, the area of the Bi(AAZTA-TATE) complex decreases as a function of time, which indicates the transchemation reaction of Bi(AAZTA-TATE) complex with AAZTA ligand according to Eq. (12). The pseudo-first-order rate constants ($k_d$) were calculated by fitting the area of Bi(AAZTA-TATE) complex-time data sets to Eq. (9) The pseudo-first-order rate constant ($k_d$) characterizing the transchelation reactions between Bi(AAZTA-TATE) and AAZTA obtained in the presence of 1.0 and 2.0 mM AAZTA are (1.7±0.1)×10$^{-7}$ s$^{-1}$ and (2.0±0.2)×10$^{-7}$ s$^{-1}$, respectively. These kinetic data clearly indicate that the [AAZTA] has practically no effect for the dissociation rate of Bi(AAZTA-TATE). It can be assumed that the rate determining step is the OH$^-$ assisted dissociation of Bi(AAZTA-TATE) complex which has been followed by the fast reaction between the free Bi$^{3+}$ and the exchanging AAZTA ligand.

The comparison of the dissociation half-life values ($t_{1/2}$=ln 2/$k_d$) of Bi(AAZTA) and Bi(AAZTA-TATE) obtained at pH=9.0 (Bi(AAZTA): $t_{1/2}$=115 hours; Bi(AAZTA-TATE): $t_{1/2}$=1138 hours at pH=9.0 and 25° C. in 0.15 M NaClO$_4$) indicates that the kinetic inertness of Bi(AAZTA-TATE) is higher by about 10 times than that of Bi(AAZTA) at close to physiological condition.

The invention claimed is:

1. A chelating compound of formula (I)

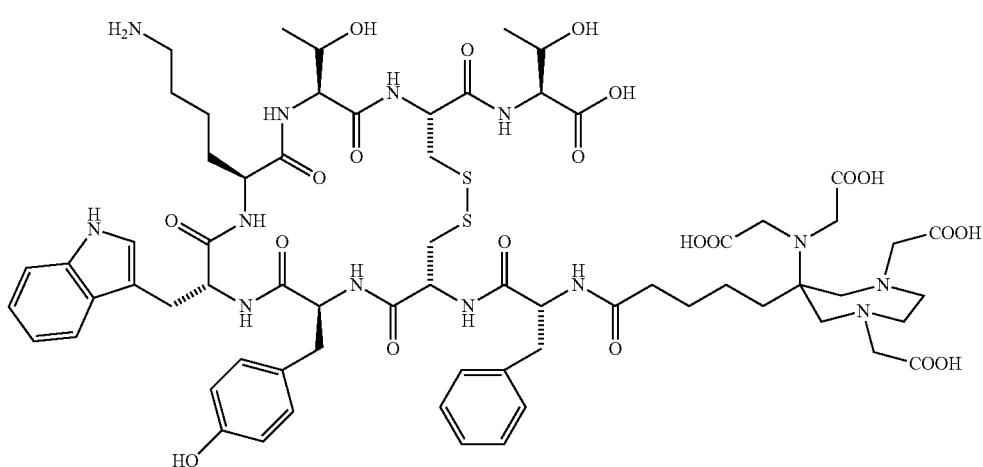

or a pharmaceutically acceptable salt thereof.

2. A metal complex comprising the chelating compound of claim 1, or its pharmaceutically acceptable salt, and a metal ion.

3. The metal complex according to claim 2, wherein the metal ion is an ion of a metal atom selected from $^{43}$Sc, $^{44}$Sc, $^{44m}$Sc, $^{47}$Sc, $^{51}$Cr, $^{52}$Fe, $^{52}$Mn, $^{52m}$Mn, $^{55}$Co, $^{58}$Co, $^{60}$Cu, $^{61}$Cu, $^{62}$Cu, $^{64}$Cu, $^{67}$Cu, $^{67}$Ga, $^{68}$Ga, $^{72}$As, $^{86}$Y, $^{88}$Y, $^{90}$Y, $^{97}$Ru, $^{99m}$Tc, $^{103}$Ru, $^{105}$Rh, $^{109}$Pd, $^{111}$In, $^{111}$Ag, $^{112}$Ag, $^{117m}$Sn, $^{140}$La, $^{141}$Ce, $^{142}$Pr, $^{149}$Pm, $^{149}$Tb, $^{152}$Tb, $^{155}$Tb, $^{153}$Sm, $^{159}$Gd, $^{161}$Tb, $^{165}$Dy, $^{166}$Dy, $^{166}$Ho, $^{167}$Tm, $^{168}$Yb, $^{175}$Yb, $^{177}$Lu, $^{186}$Re, $^{188}$Re, $^{199}$Au, $^{203}$Pb, $^{212}$Pb, $^{205}$Bi, $^{206}$Bi, $^{210}$Bi, $^{211}$Bi, $^{212}$Bi, $^{213}$Bi and $^{214}$Bi.

4. The metal complex according to claim 2, wherein the metal ion is an ion of a metal atom selected from $^{43}$Sc, $^{44m}$Sc, $^{44}$Sc, $^{52}$Fe, $^{52}$Mn, $^{52m}$Mn, $^{60}$Cu, $^{61}$Cu, $^{62}$Cu, $^{64}$Cu, $^{67}$Ga, $^{68}$Ga, $^{72}$As, $^{86}$Y, $^{99m}$Tc, $^{111}$In, $^{152}$Tb, $^{155}$Tb, $^{199}$Au and $^{203}$Pb.

5. The metal complex according to claim 2, wherein the metal ion is an ion of a metal atom selected from $^{47}$Sc, $^{67}$Cu, $^{88}$Y, $^{90}$Y, $^{97}$Ru, $^{103}$Ru, $^{105}$Rh, $^{109}$Pd, $^{111}$Ag, $^{112}$Ag, $^{117m}$Sn, $^{140}$La, $^{149}$Pm, $^{149}$Tb, $^{153}$Sm, $^{161}$Tb, $^{165}$Dy, $^{166}$Dy, $^{166}$Ho, $^{167}$Tm, $^{168}$Yb, $^{175}$Yb, $^{177}$Lu, $^{186}$Re, $^{188}$Re, $^{199}$Au, $^{205}$Bi, $^{206}$Bi, $^{210}$Bi, $^{211}$Bi, $^{212}$Bi, $^{212}$Pb, $^{213}$Bi and $^{214}$Bi.

6. The metal complex according to claim 3, wherein the metal ion is an ion of $^{44}$Sc, $^{47}$Sc, $^{68}$Ga, $^{177}$Lu, $^{212}$Pb or $^{213}$Bi.

7. The compound according to claim 1, wherein the pharmaceutically acceptable salt comprises the compound of formula I with at least one carboxylic group in ionic form and an inorganic or organic cation.

8. The compound according to claim 1, wherein the pharmaceutically acceptable salt comprises the compound of formula I with at least one amino group in ionic form and an inorganic or organic anion.

9. A method of diagnostic imaging, comprising administering the metal complex of claim 4 to a patient and detecting the metal complex by obtaining an image of the patient.

10. The method of claim 9, further comprising detecting a neuroendocrine tumor.

11. A method of treating a tumor in a patient, comprising administering an effective amount of the metal complex of claim 5 to the patient.

12. The method according to claim 11, wherein the tumor is a neuroendocrine tumor.

13. A pharmaceutical composition comprising the chelating compound according to claim 1 in admixture with a pharmaceutically acceptable excipient.

14. A pharmaceutical composition comprising the metal complex according to claim 2, in admixture with a pharmaceutically acceptable excipient.

15. The method of claim 9, wherein the image is obtained by Positron Emission Tomography (PET) or Single Photon Emission Computerized Tomography (SPECT).

16. The metal complex according to claim 6, wherein the metal ion is an ion of $^{44}$Sc, $^{68}$Ga, or $^{213}$Bi.

17. The metal complex according to claim 16, wherein the metal ion is $^{68}$Ga.

18. The metal complex according to claim 16, wherein the metal ion is $^{44}$Sc.

19. The metal complex according to claim 16, wherein the metal ion is $^{213}$Bi.

* * * * *